(12) United States Patent
Weatherall et al.

(10) Patent No.: US 9,841,448 B2
(45) Date of Patent: Dec. 12, 2017

(54) RESONANT SYSTEM AND METHOD OF DETERMINING A DIELECTRIC CONSTANT OF A SAMPLE

(71) Applicant: Battelle Memorial Institute, Columbus, OH (US)

(72) Inventors: James C. Weatherall, Linwood, NJ (US); Jeffrey Barber, Vineland, NJ (US); Barry T. Smith, Egg Harbor City, NJ (US)

(73) Assignee: Battelle Memorial Institute, Columbus, OH (US)

( * ) Notice: Subject to any disclaimer, the term of this patent is extended or adjusted under 35 U.S.C. 154(b) by 94 days.

(21) Appl. No.: 14/943,362

(22) Filed: Nov. 17, 2015

(65) Prior Publication Data

US 2016/0146872 A1  May 26, 2016

Related U.S. Application Data

(60) Provisional application No. 62/083,561, filed on Nov. 24, 2014.

(51) Int. Cl.
*G01R 27/26* (2006.01)
*G01N 22/00* (2006.01)

(52) U.S. Cl.
CPC ......... *G01R 27/2664* (2013.01); *G01N 22/00* (2013.01)

(58) Field of Classification Search
CPC ...... G01N 27/023; G01N 22/00; G01N 22/04; G01N 27/02; A61B 5/0031
USPC ........................................................ 324/633
See application file for complete search history.

(56) References Cited

U.S. PATENT DOCUMENTS

| | | | | |
|---|---|---|---|---|
| 2,576,186 A | * | 11/1951 | Malter | H01P 1/08 315/39 |
| 2,890,419 A | * | 6/1959 | Hagan | H01J 17/04 333/13 |
| 3,214,684 A | * | 10/1965 | Everitt | H01P 5/04 324/318 |
| 3,384,814 A | * | 5/1968 | Stinehelfer | H01P 7/06 324/636 |
| 4,691,179 A | * | 9/1987 | Blum | H01P 1/2056 333/202 |

OTHER PUBLICATIONS

Yang, Li-Jun, et al. "Experimental and theoretic study of the dielectric properties of ethanol+ methanol mixtures." Journal of solution chemistry 39.4 (2010): 473-481.*

(Continued)

*Primary Examiner* — Jermele M Hollington
*Assistant Examiner* — Christopher McAndrew
(74) *Attorney, Agent, or Firm* — Diederiks & Whitelaw, PLC (57) ABSTRACT

The present invention pertains to a resonant cavity system, more specifically, a resonant system for measuring the dielectric constant of a sample and its method of use. The system and method provide for holding sample materials, which can be in solid, liquid, or powder form, and for reducing the size of the requisite cavity for measurement. The construction incorporates waveguide flange connectors to seal the electromagnetic cavity, which facilitates the measurement of low-loss materials. The design for signal input enables the use of standard calibration techniques and measurement.

20 Claims, 9 Drawing Sheets

(56) References Cited

OTHER PUBLICATIONS

Venkatesh, M. S., and G. S. V. Raghavan. "An overview of dielectric properties measuring techniques." Canadian biosystems engineering 47.7 (2005): 15-30.*

Poplavko, Yuriy, et al. "Waveguide technique for ferroelectric bulk and film microwave study." ARFTG Conference Digest, Spring 2003. 61st. IEEE, 2003.*

Kajfez, D., et al. "Uncertainty analysis of the transmission-type measurement of Q-factor." IEEE Transactions on Microwave Theory and Techniques 47.3 (1999): 367-371.*

Bechteler, A. Sevinc Aydinlik, and Levent Sevgi. "Millimeter waveband semisymmetrical groove guide resonators." IEEE Microwave Magazine 5.3 (2004): 51-60.*

Abu-Teir, M., et al. "Local contactless measurement of the ordinary and extraordinary Hall effect using near-field microwave microscopy." Applied physics letters 80.10 (2002): 1776-1778.*

Agilent Technologies, "*Agilent Basics of Measuring the Dielectric Properties of Materials*", 2006.

Barber et al., "*Millimeter Wave Measurements of Explosives and Simulants*", Proc. of SPIE, vol. 7670, 2010.

"*IPC-TM-650 Test Methods Manual*", Jan. 2007.

Kim et al., "*Electromagnetic Metrology on Concrete and Corrosion*", Journal of Research of the National Institute of Standards and Technology, vol. 116, No. 3, pp. 655-669, 2011.

"*Software for Electromagnetic Design—Hardware for Measurement of Electromagnetic Properties of Materials*" www.qwed.eu/resonators_tw01, Sep. 17, 2013.

Weatherall et al., "*Dielectric Measurements HME and Design of High Fidelity Simulants in UHF Band*", U.S. Department of Homeland Security, Dec. 2012. (Edited and Redacted for Public Release).

Weatherall et al., "*Measurement of the Reflectivity and Absorptivity of Liquids, Powders, and Solids at Millimeter Wavelengths Using Dielectric Detection by a Resonator-Post Fixture Between Parallel Conducting Plates*", Proc. of SPIE, vol. 8019, 2011.

* cited by examiner

RESONANT SYSTEM AND METHOD OF DETERMINING A DIELECTRIC CONSTANT OF A SAMPLE

CROSS REFERENCE TO RELATED APPLICATIONS

This application claims the benefit of U.S. Provisional Patent Application Ser. No. 62/083,561, which was filed on Nov. 24, 2014 and titled "Fixtures for Solids, Liquids, and Powders for the Measurement of Electromagnetic Properties of Materials and the Miniaturization of a Resonant Cavity Measurement Apparatus". The entire content of this application is incorporated by reference.

STATEMENT REGARDING FEDERALLY SPONSORED RESEARCH OR DEVELOPMENT

This invention was made with government support under Contract No. HSHQDC-12-F-00048 awarded by the Department of Homeland Security. The government has certain rights in the invention.

BACKGROUND OF THE INVENTION

There is a prevailing need for the detection of explosives, particularly in the aviation industry, but also in other mass transit modes of transportation. More specifically, there exists a need for technology to detect various explosives and hazardous materials that are in liquid or powdered form and also to distinguish hazardous materials, such as homemade explosives, acids, oxidizers, and flammable liquids from benign materials, such as medical liquids, baby formula, beverages, lotions, hygiene products, contact lens solutions and the like.

A material's dielectric constant (permittivity) is determined by measuring its response to a harmonic electric field generated, for example, by a vector network analyzer. Quantifying a material's dielectric constant at selected frequencies or within a frequency range is important for applications relating to optical properties and power transmission. Applications of particular interest include the detection of explosive materials in personnel screening systems (such as millimeter-wave portals used in airports) and the design of explosive simulants that reproduce the optical properties of explosives for the purpose of testing and system validation of various detection systems. Dielectric detection is also used for quality control in chemical, medical, and pharmaceutical applications, such as testing for chemical change or purity or monitoring the curing and aging of concrete.

The dielectric constant of a material can change based on the frequency of applied electromagnetic radiation. Various laboratory techniques have been applied to measure the dielectric constant of materials in radar, microwave, and millimeter-wave frequency bands, including: free-space measurements, performed by transmission and reflection of radiation through a planar slab of material between two transmitting horns; coaxial probes, which measure a reflected signal due to fringing fields from a coaxial line in contact with the material; and waveguide cells, where transmission and reflection through a sample of material loaded into a waveguide or coaxial line is measured. The aforementioned techniques rely on optical effects at the material interfaces to detect the dielectric constant.

Resonant techniques have also been used to measure the dielectric constant of materials. Resonant techniques are different from optical techniques in the sense that the material is incorporated into the electromagnetics of the system. Resonant methods provide the most accurate measurement of the complex dielectric constant of low-absorption materials, i.e., where the imaginary component of the dielectric constant, related to the absorption loss, is small.

Sample configuration is important in resonant systems. Commercial systems based on resonators most often require planar sheets or discs to be inserted into a resonant cavity. This type of configuration is not suited for loose powders or liquids or practical for all materials. However, prior art systems have been developed including fixtures for resonator systems that hold liquids and powders in addition to solids. The dielectric samples have been held in fixtures of particular geometric shape and dimension. Furthermore, the fixtures are integrated into, and form a significant aspect of, the resonant system.

A prior fixture illustrates the idea of measuring the dielectric constant of a sample in a resonant-post system designed for use with electromagnetic radiation at 20-25 GHz in which the resonant post is modified to enclose a small sample. In this configuration, the post is situated between two flat conducting plates and the arrangement is referred to as an "open resonator". The fixture is a low-loss plastic cylinder, which comprises the post and sample holder. More details of this "open resonator" can be found in the article Weatherall, James C., Barber, Jeffrey, Brauer, Carolyn S., and Barry T. Smith. "Measurement of the reflectivity and absorptivity of liquids, powders, and solids at millimeter wavelengths using dielectric detection by a resonator-post fixture between parallel conducting plates." *Proceedings of SPIE* 8019.80190F (2011): 1-8, which is incorporated herein by reference. However, such an open resonator system has many disadvantages. For example, in the open resonator, electromagnetic fields have numerous harmonic modes, which are present in a large spectrum of overlapping modes, and the fields, which are not contained, leak out of the unit, thus radiating the environment. Additionally, the open resonator is calibrated indirectly and is, therefore, difficult to accurately calibrate with reference standards. As a result, there exists a need in the art for a resonator system for measuring dielectric constants of materials that does not suffer from the above-described deficiencies.

SUMMARY OF THE INVENTION

The present invention pertains to a resonant cavity system, more specifically, a resonant system for measuring a dielectric constant of a sample. The system comprises a device for holding a sample including a resonant waveguide formed with a cavity. The cavity is configured to hold a fixture, and the fixture is configured to hold a sample. The system also includes a network analyzer including a signal source configured to send electromagnetic radiation toward a sample, a radio frequency detector configured to sense electromagnetic radiation reflected from or transmitted through a sample, and a processor configured to determine a dielectric constant of a sample based on the sensed electromagnetic radiation.

In a preferred embodiment, the fixture is plastic or ceramic, and the resonant waveguide is metal. The fixture is configured to hold a sample in a center of the cavity. The fixture is also configured to fill substantially all of the cavity. In another preferred embodiment, the fixture has a recess, and a sample holder is provided for holding a sample within the recess. A transmitting waveguide is connected to the resonant waveguide. In one embodiment, the transmitting waveguide has one coaxial port that is connected to one port on the network analyzer, and the transmitting waveguide is configured to capture electromagnetic radiation that reflects from a sample. In another embodiment, the transmitting waveguide has two coaxial ports that are connected to two ports on the network analyzer, and the transmitting waveguide is configured to capture electromagnetic radiation that is transmitted through a sample. Preferably, the transmitting waveguide is rectangular and has a central aperture, while the resonant waveguide is circular and includes an aperture aligned with the central aperture.

The present invention is also directed to a method of determining a dielectric constant comprising placing a sample in a fixture so that the sample is encased in the fixture and is part of a resonator in a resonant system. A harmonic electric field is applied to the sample, and the harmonic electric field reflected from or transmitted therethrough is measured. The dielectric constant of the sample is determined at harmonic frequencies of the electromagnetic radiation. Preferably, the sample is precisely placed within the fixture. The method also includes reducing a wavelength of the electromagnetic radiation with the fixture and setting a frequency at which the system measures the dielectric constant of the sample by changing the size and geometry of the fixture. Preferably, the method also includes minimizing the sample size by changing the size and geometry of the fixture.

The method and system provides for holding sample materials, which can be in solid, liquid, or powder form, and for reducing the size of the requisite cavity for measurement. A complete resonant cavity system for measuring the complex dielectric constant at 25 GHz is shown as a preferred embodiment. However, the design is scalable to other frequencies. The construction incorporates waveguide flange connectors to seal the electromagnetic cavity, which facilitates the measurement of low-loss materials. A two-port design for signal input enables the use of standard calibration techniques and measurement.

In any case, additional objects, features and advantages of the invention will become more readily apparent in from the following detailed description of the invention when taken in conjunction with the provided drawings.

DETAILED DESCRIPTION OF THE INVENTION

Detailed embodiments of the present invention are disclosed herein. However, it is to be understood that the disclosed embodiments are merely exemplary of the invention that may be embodied in various and alternative forms. The figures are not necessarily to scale, and some features may be exaggerated or minimized to show details of particular components. Therefore, specific structural and functional details disclosed herein are not to be interpreted as limiting, but merely as a representative basis for teaching one skilled in the art to employ the present invention.

Figure 1A:
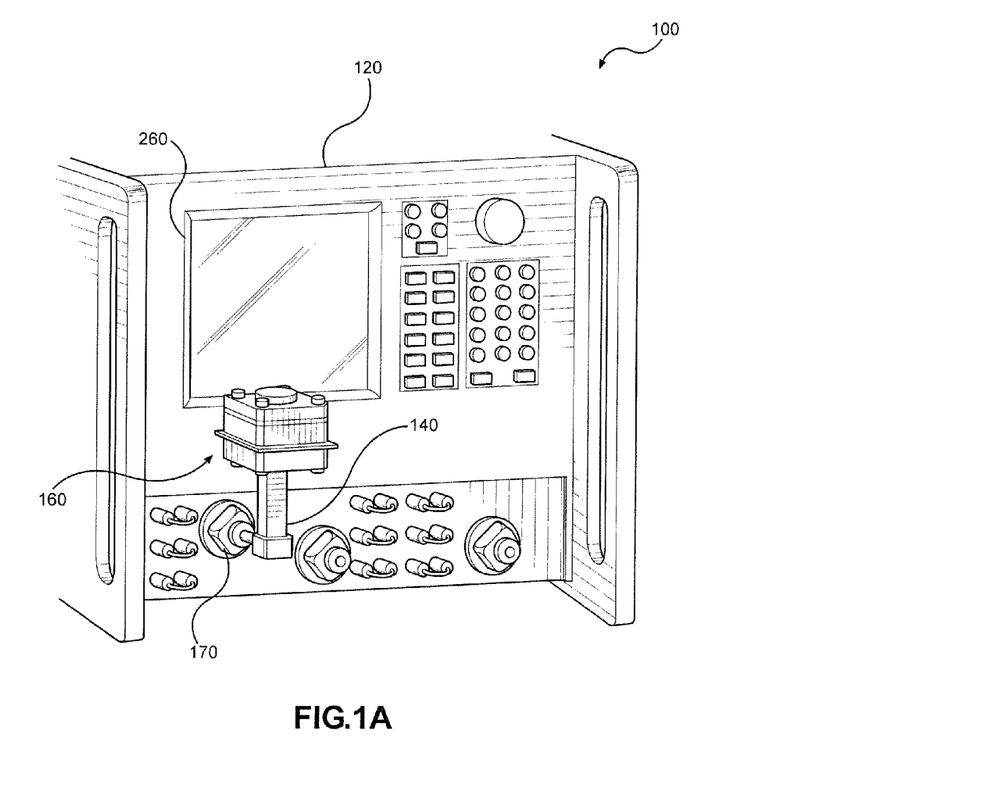
FIG. 1A depicts a device for holding a sample material connected to a vector network analyzer according to a preferred embodiment of the invention.
Figure 1B:
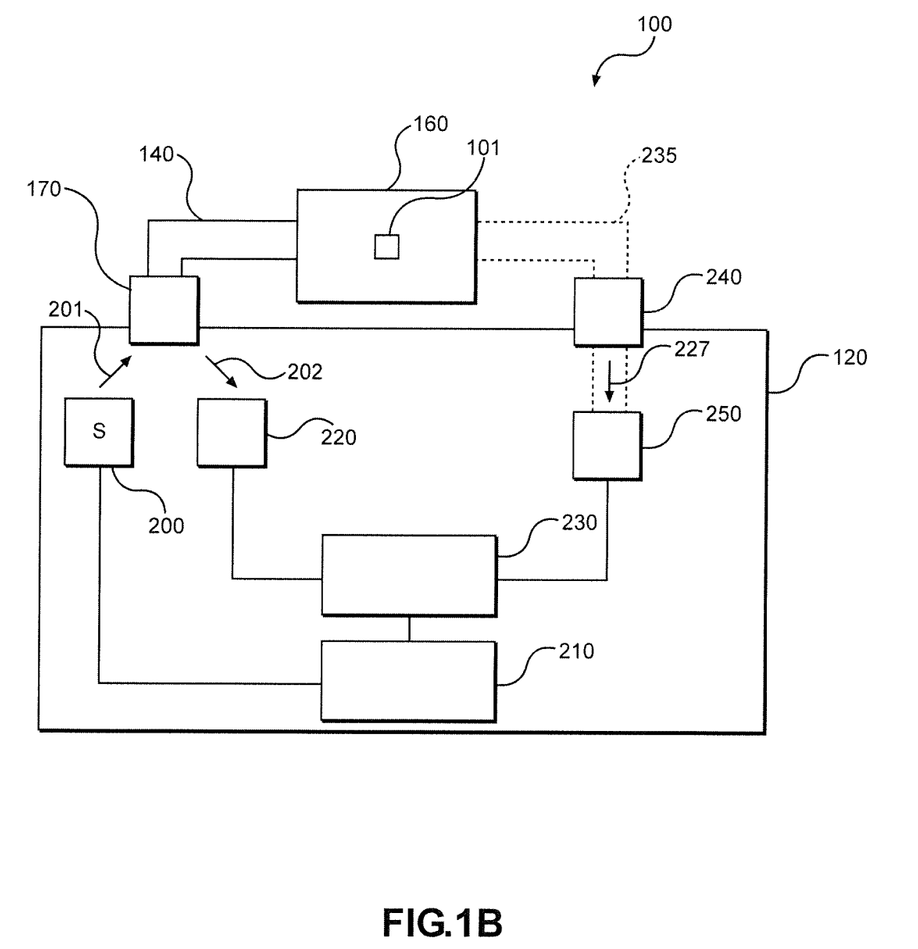
FIG. 1B is a schematic of the arrangement of FIG. 1A.
Figure 1C:
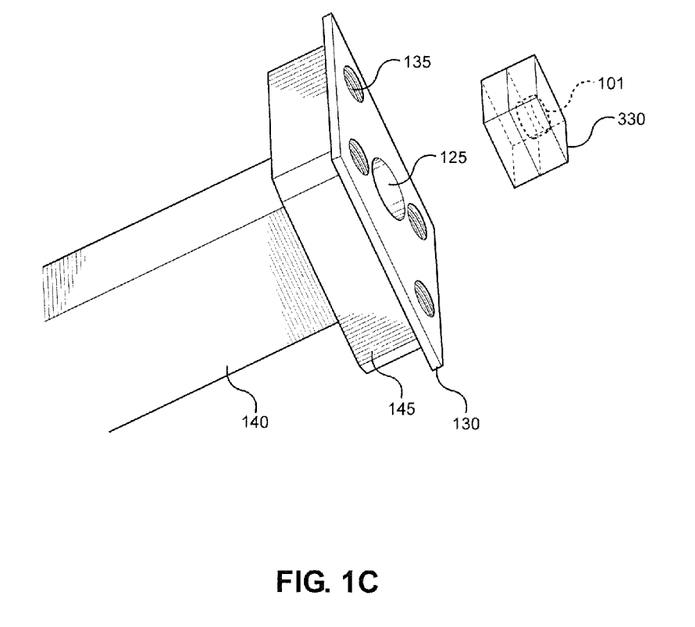
FIG. 1C is an exploded view of a portion of the device of FIG. 1A.

As depicted in FIGS. 1A-C, the present invention pertains to a resonant cavity based system 100 for measuring the dielectric constant of a sample 101 of material. System 100 has three main components: a network analyzer 120, a transmission waveguide 140 and a device 160 for holding sample 101. Preferably, transmission waveguide 140 is connected to network analyzer 120 at a port 170 and to device 160 and is arranged to transmit electromagnetic signals from network analyzer 120 to sample 101 mounted in device 160.

Network analyzer 120 is schematically shown in FIG. 1B and includes a signal source 200 for generating an electromagnetic radiation signal at various frequencies. Signal source 200 is controlled by a processor 210, which preferably controls the different functions of network analyzer 120. Signal source 200 is configured to send a source signal out port 170 through waveguide 140 to device 160. When the source signal hits sample 101 both a reflected signal 202 and a transmitted signal 227 may be generated. A reflected signal 202 will pass back through waveguide 140 to port 170 so that a detector 220 can detect reflected signal 202. Preferably, detector 220 also detects a source signal 201 and sends information regarding source signals 201 and reflected signals 202 to a receiver 230 and ultimately to processor 210. Optionally, transmitted signal 227 may pass through a waveguide 235 to a port 240 and then be detected by a detector 250, which sends information regarding the transmitted signal 227 to receiver 230. When signal source 200 sends source signal 201 at a frequency, the information sent to receiver 230 includes the magnitude and phase data at that frequency. Source 200 is then stepped up to the next frequency and the magnitude and phase data at the next frequency is processed. The reflection and transmission data may then be plotted on a display 260 as a function of frequency. Network analyzers are commercially available. For example, Agilent Technologies makes a network analyzer model PNA-X that can be used with the invention.

Transmission waveguide 140 is preferably a metal conduit configured to transmit source 201 and reflected signals 202 between port 170 and device 160. While shown as only being attached to one port 170 in FIG. 1A, a transmission waveguide may be connected to two ports as shown in FIG. 1B and discussed in more detail below with respect to an additional embodiment of the invention.

In FIG. 1C, the portion of waveguide 140 that meets device 160 is shown (although only part of device 160 is shown). Waveguide 140 includes a flange 145, which is coupled to a plate 130. Plate 130 has an iris or aperture 125 so that the electromagnetic radiation signal can pass to and from sample 101 located in a plastic fixture 330. Plate 130 also has a plurality of holes (one of which is labeled 135) for receiving coupling elements, such as bolts, as will be described in further detail in connection with FIG. 2.

Figure 2:
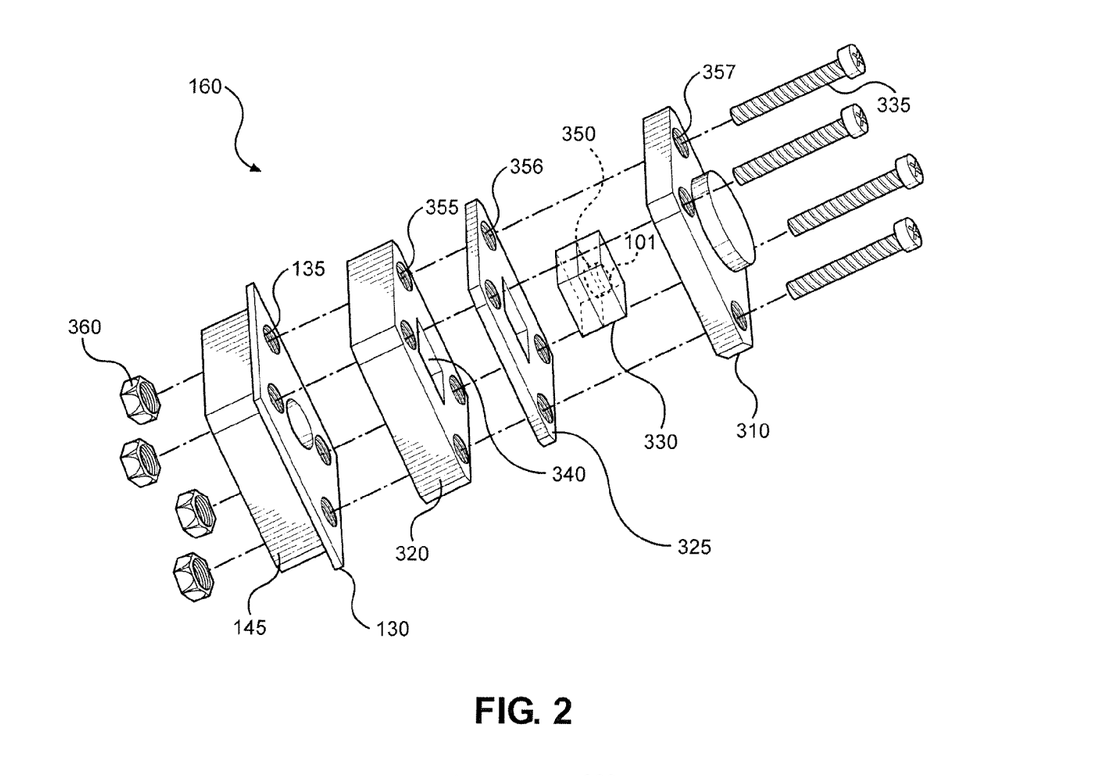
FIG. 2 is an exploded view of the device of FIG. 1.

Device 160 is illustrated in more detail in FIG. 2 in an exploded configuration showing an upper housing 310, a lower housing 320 and plastic fixture 330. Upper housing 310 and lower housing 320 are preferably made of metal and form a cavity 340. Optionally lower housing 320 may have an extra segment 325 to facilitate disassembly of cavity 340. Cavity 340, which is totally enclosed in metal, operates at multiple modes. A receiver 350 (best seen in FIG. 3) holds a sample 101 and is mounted in plastic fixture 330, which fills the entire cavity 340. As mentioned above, a plurality of coupling elements (one of which is labeled 335) is used to securely couple the portions of device 160 to one another. As illustrated, the coupling elements are bolts, although other coupling elements can, of course, be used. The coupling elements extend through holes of device 160 (three of which are labeled 355-357) and are secured by nuts (one of which is labeled 360).

Figure 3:
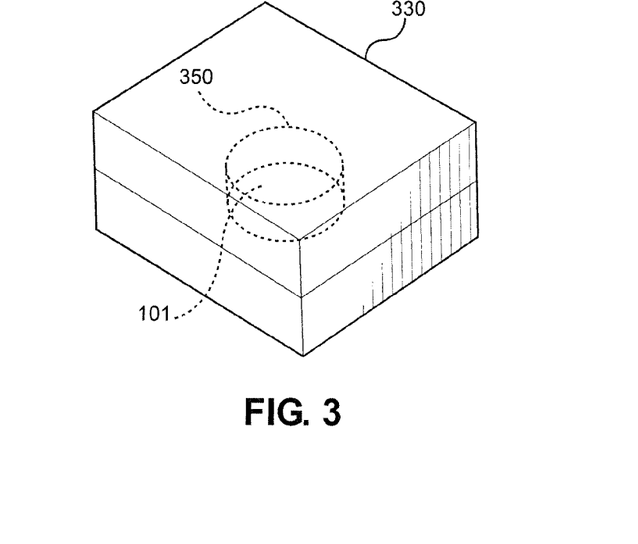
FIG. 3 shows a plastic insert for the device of FIG. 2.
Figure 4A:
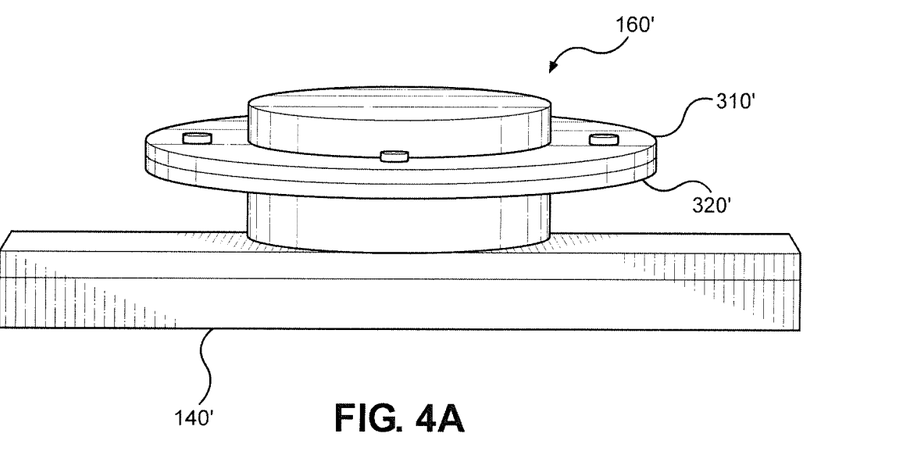
FIG. 4A shows a device for holding a sample material connected to a waveguide according to another embodiment of the invention.
Figure 4B:
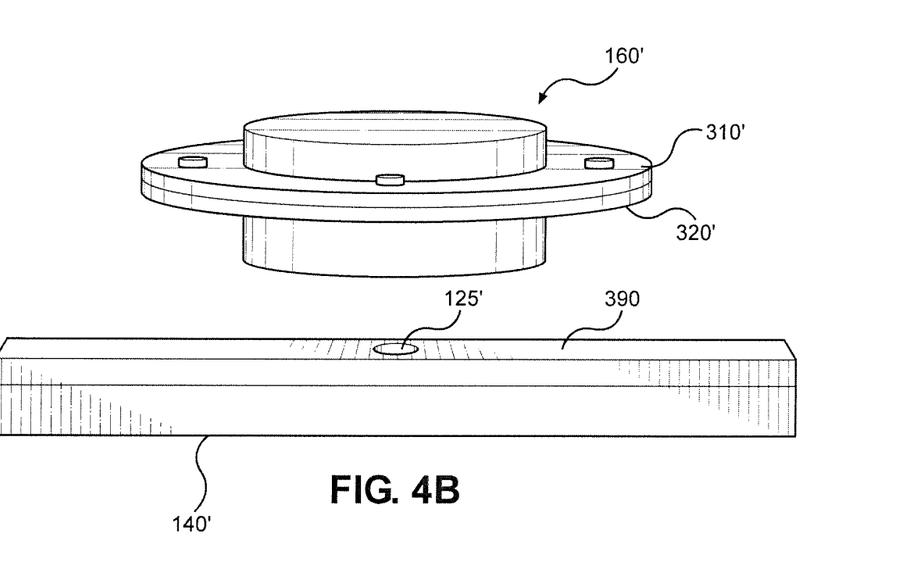
FIG. 4B shows the device separated from the waveguide of FIG. 4A.

The role of plastic fixture 330 is to enable the precise placement of sample 101 for measurement. The plastic allows the dimensions of cavity 340 to be varied. For example, plastic fixture 330, in a certain arrangement and using certain materials, will reduce the electromagnetic wavelength by approximately 40% when compared to an empty cavity and, hence, the size of cavity 340 as well. The electromagnetic wavelength scales as the inverse square root of the dielectric constant of the plastic. By using materials, such as various ceramics, with higher dielectric constants to form fixture 330, it is possible to decrease the size by several hundred percent or more compared to an empty cavity. Iris 125 couples signal 200 sent into waveguide 140, to cavity 340. Preferably the diameter of iris 125 is set to be large enough to observe return signal 202 but not so large as to perturb a cavity mode. Iris 125 is preferably centered in plate 130 to reduce the number of modes excited in the cavity, which is useful to avoid resonances, which overlap in frequency.

In the case of a resonator system, fixture 330 replaces what would be the post in a "conventional" resonant-post system. In such a system, the post is usually a solid, whole cylinder formed of the sample material. By contrast in the current invention, fixture 330 enables positioning the sample in the exact center of cavity 340 for optimal interaction with the electric field. Encasing sample 101 within fixture 330 provides certain advantages: the size (volume) of sample 101 can be minimized, which is useful when the sample is dangerous or expensive; sample 101 can be sealed for quality control and ease of handling; and the frequency at which the measurement is obtained is fixed by the geometry and dielectric constant of fixture 330 and does not vary substantially with the geometry and dielectric constant of sample 101. Sample 101 and fixture 330 have a geometry that is amenable to design modification for sensitivity and frequency of measurement: a larger fixture resonates at a lower frequency, and a smaller sample can be used to accommodate more absorptive materials.

For the above arrangement, the resonator frequency shift and frequency width are measured in standard ways with network analyzer 120. Relating the measurement to the dielectric constant is accomplished either through a mathematical formulation that is specific for the dielectric geometry or by computer simulation with commercial software, such as COMSOL, which may reside in processor 210.

FIGS. 4A, 4B, 5A, and 5B show an alternative embodiment of the invention wherein a device 160', analogous to device 160 of the embodiment shown in FIGS. 1A, 1B and 2, forms a resonant cavity 340' between an upper housing 310' and a lower housing 320' connected to each other by a flange connection. Preferably, resonant cavity 340', formed in device 160', is shaped as a circular waveguide. Device 160' is preferably coupled to network analyzer 120 with a rectangular waveguide 140', which is connected to cavity 340' through an aperture in a cavity wall (not shown) and an iris 125' in waveguide wall 390. Determination of the dielectric constant is accomplished by two-port measurement of the signal input through rectangular waveguide 140'. As best seen in FIG. 1B, waveguide 235 can extend to port 240 in network analyzer 120. While not shown in FIGS. 4A and 4B, rectangular waveguide 140' can connect to ports 170 and 240 in an analogous manner. The measurement system uses a commercial rectangular waveguide. Waveguide 140' is coupled to cavity 340' with small circular iris 125' centered in broad wall 390 of waveguide 140'. In this design, iris 125' is 1.5 mm in diameter, and waveguide wall 390 and cavity end-wall 380 thickness (total) is 2 mm. Waveguide 140' is terminated with standard waveguide-to-coax adapters to connect to network analyzer 120. Because the system has two terminals, the measurement device can be calibrated with a full two-port calibration at the waveguide terminations. The embodiment of FIGS. 4A, 4B, 5A, and 5B represents a system for measuring a dielectric constant of a sample material at 25 GHz, as in FIG. 1. The body of device 160' forming cavity 340' is preferably fashioned to form a circular waveguide and is preferably fabricated from a commercial stock.

Figure 5A:
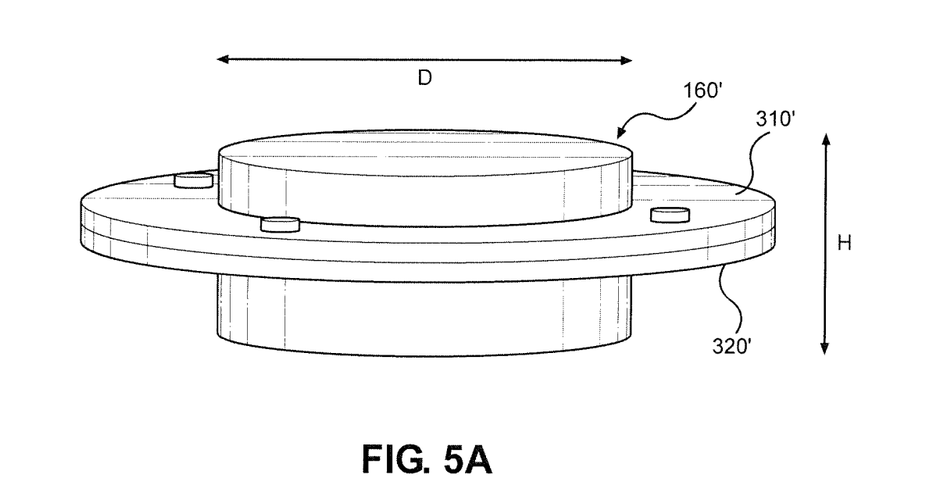
FIG. 5A shows the device of FIG. 4A.
Figure 5B:
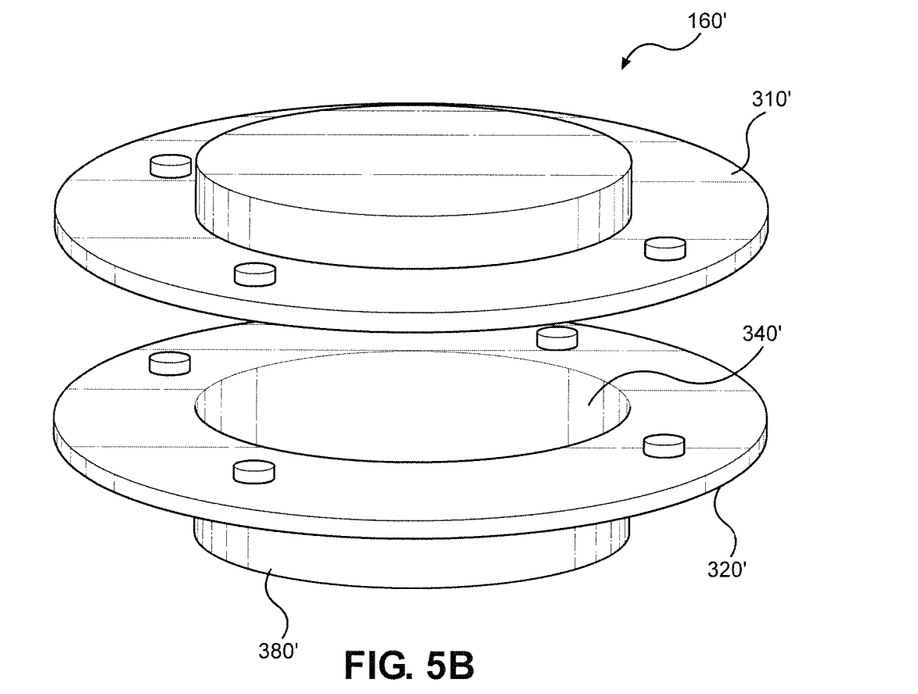
FIG. 5B shows an exploded view of the device in FIG. 5A.
Figure 6A:
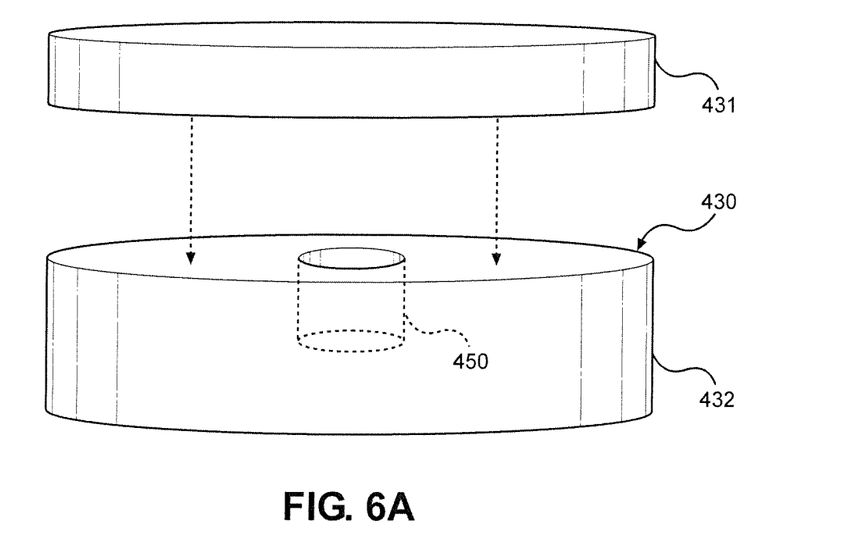
FIG. 6A shows an exploded view of an insert from FIG. 4A.
Figure 6B:
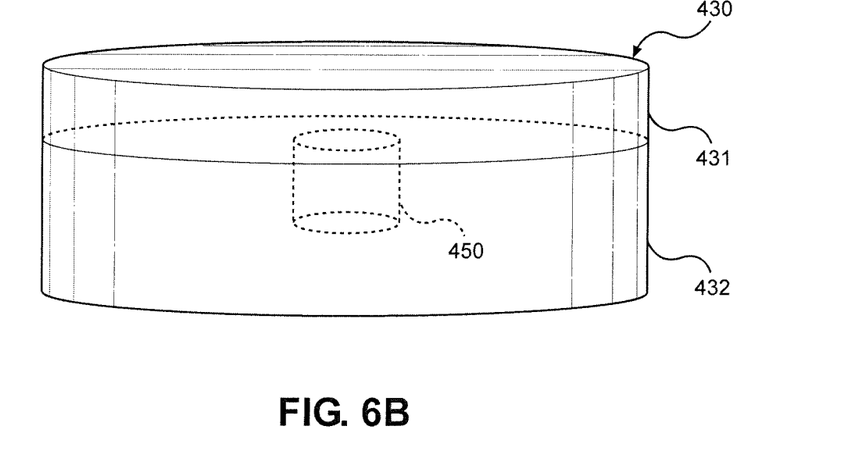
FIG. 6B shows the insert from FIG. 4A.

A fixture 430 is shown in FIGS. 6A and 6B having a top portion 431 and a bottom portion 432. Bottom portion 432 is formed with a recess 450 for containing a sample. Once a sample is placed in recess 450, top portion 431 is placed on bottom portion 432 as shown in FIG. 6B. Fixture 430 is then placed in cavity 340'. Device 160' comes apart, as shown in FIG. 5B, for placement of fixture 430 and the sample within cavity 340'. Also, it is preferable that fixture 430 fills the empty space inside cavity 340'. Characteristic dimensions of device 160' are provided in Table 1 assuming that fixture 430 has a dielectric constant of 2.54. With the use of commercial waveguide components, cavity 340' can be sealed using a standard waveguide-to-waveguide interface. This embodiment provides for electromagnetic isolation and repeatability of results. FIGS. 6A and 6B show plastic fixture 430 that fits inside cavity 340' (either removably or permanently attached to cavity 340'). The plastic is preferably a low-loss material such as Rexolite (a cross-linked polystyrene), polyethylene, Teflon, or similar plastic.

TABLE 1

Design Parameters for 25 GHz Cavity with Polyethylene Plastic Fixture

| | | |
|---|---|---|
| cavity inner diameter | D | 2.29 cm |
| Cavity height | H | 1 cm |
| Upper cavity segment height | | 3/8 H |
| Bottom cavity segment height | | 5/8 H |
| Flange diameter | | 3.81 cm |

Figure 7A:
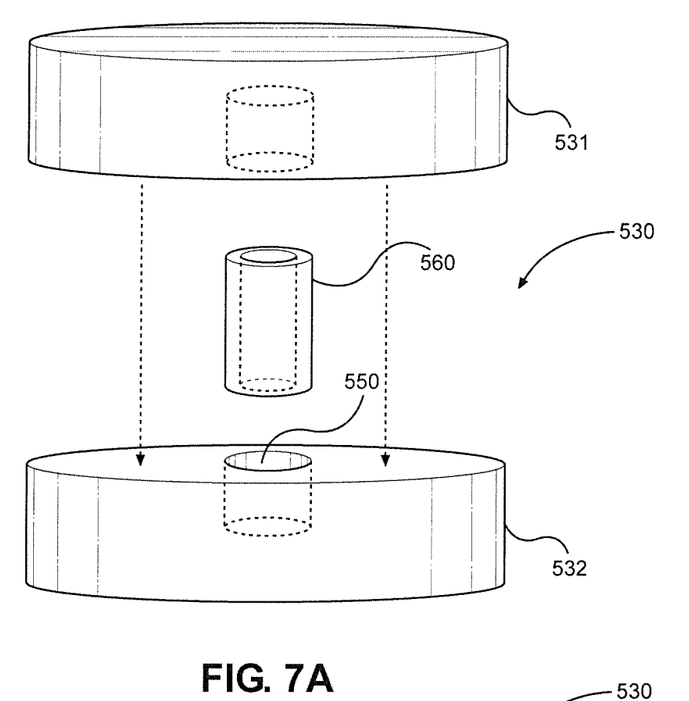
FIG. 7A shows an exploded view of an insert according to another embodiment of the invention.
Figure 7B:
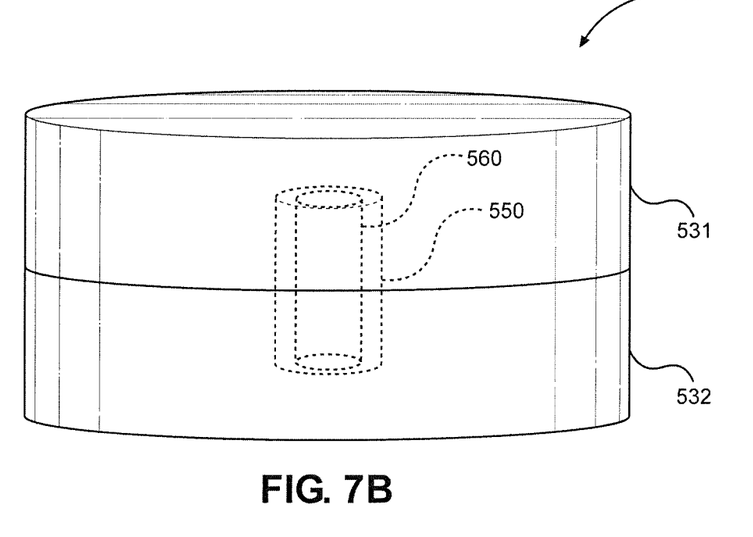
FIG. 7B shows the insert of FIG. 7A.

FIGS. 7A and 7B show a fixture 530 designed to provide a larger cavity such as a low-frequency cavity. Fixture 530 is similar to fixture 430 and has a top portion 531 and a bottom portion 532. However, a recess 550 is formed in both top portion 531 and bottom portion 532. Also, a separate plastic sample holder 560 is used that is preferably embedded into the larger plastic structure (i.e., top portion 531 and bottom portion 532) as shown in FIG. 7B.

As conceived, cavity 340 resonates at 25 GHz in the TM022 mode. Other modes can be used for measurement, but this mode is suited for coupling with an axial aperture and placement of the sample in the center of cavity 340. The cavity resonant spectrum is determined by the cavity height and diameter and the dielectric constant of the interior.

Figure 8:
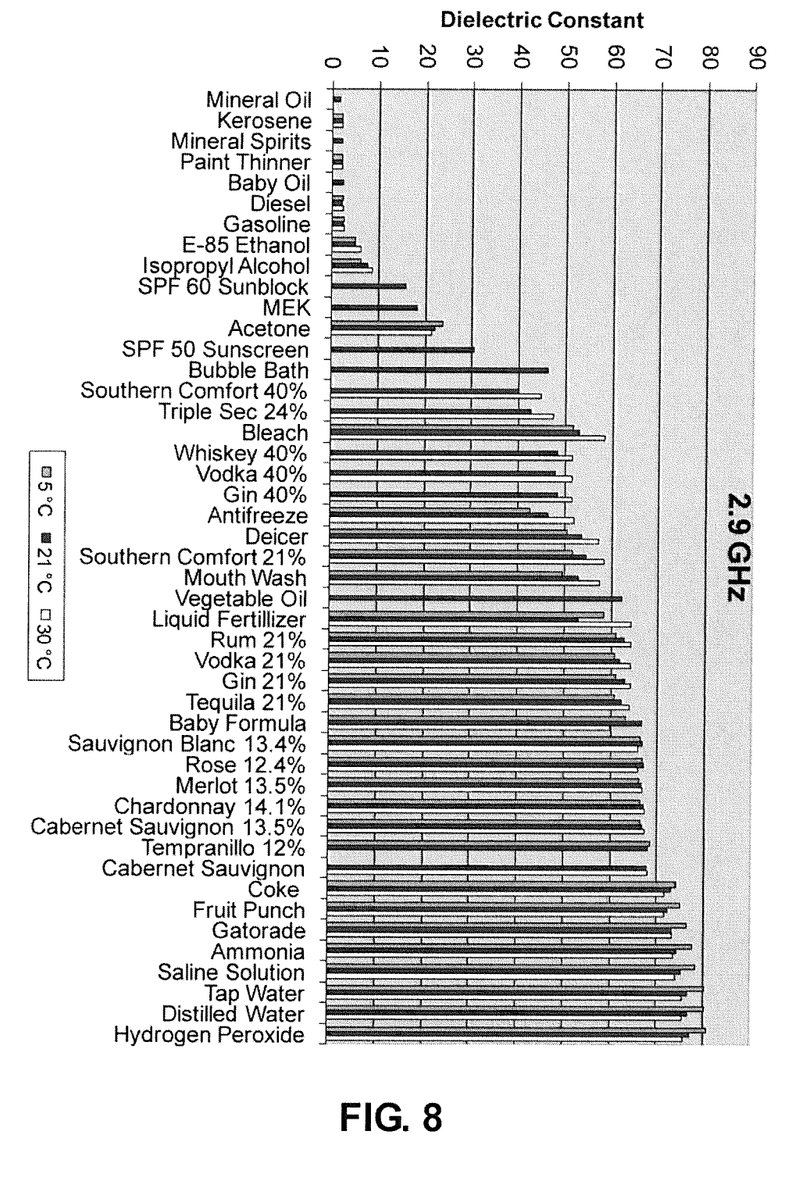
FIG. 8 is graph showing some known dielectric constants for various materials.

Dielectric constants of many liquids are provided as plots in FIG. 8. The plots were obtained by employing an Agilent 85070E dielectric probe, its associated software and an Agilent E86363B Precision Network Analyzer.

With the embodiments shown in FIGS. 1A-7B, a solid, liquid or powder sample can be encapsulated into a standardized sample holder so that sample preparation and integrity are separated from the measurement process. Furthermore, this arrangement provides the ability to scale the sample holder size for measurement at desired frequencies. This arrangement also provides for minimizing the size of the resonant cavity. In addition, the embodiment in FIG. 4A shows a throughput system that can be calibrated with standard two-port techniques.

A preferred embodiment described herein is a specific example of a system using a resonant cavity, totally enclosed in metal, operating at multiple modes between 200 and 2000 MHz and having a plastic fixture that fills the entire cavity. The role of the plastic fixture is to enable the precise placement of a sample for measurement. The plastic also affects the dimensions of the cavity. In this example, the effect of the plastic fixture is to reduce the electromagnetic wavelength by approximately 40% and, hence, the size of the cavity as well. The electromagnetic wavelength scales as the inverse square root of the dielectric constant of the plastic. By using materials with higher dielectric constants for the fixture composition (such as various ceramics), it is possible to decrease the size by several hundred percent or more. With respect to the resonator, the fixture is used as the post in a "conventional" resonant-post system, where usually the post is a solid, whole cylinder comprised in total of the sample material. With respect to the cavity, the fixture provides a method of positioning the sample in the exact center of the cavity for optimal interaction with the mode electric field. Encasing the sample within the fixture provides certain advantages: the size, i.e., volume of the sample can be minimized, which is useful when the sample is dangerous or expensive; the sample can be sealed for quality control and ease of handling; and the frequency at which the measurement is obtained is fixed by the geometry and dielectric constant of the fixture and does not vary substantially with the sample. The sample and fixture geometry is amenable to design modification for sensitivity and frequency of measurement: a larger fixture resonates at a lower frequency, and a smaller sample can be used to accommodate more absorptive materials.

For both of the post-resonator and cavity systems, the resonator frequency shift and frequency width are measured in standard ways with the network analyzer. Relating the measurement to the dielectric constant is accomplished either through mathematical formulation, which is specific for the dielectric geometry, or by computer simulation with commercial software, such as COMSOL.

While certain of the above structure is describe as being circular or rectangular, it should be understood that the structures need not be perfectly circular or rectangular. In particular, for purposes of the present invention, circular and rectangular structures include those structures that are intended to be perfectly circular or rectangular but that are not due to the inherent limitations of the applicable manufacturing processes. In addition, the terms "generally circular" and "generally rectangular" include oval-, parallelogram- and trapezoid-shaped structures. Similarly, while the fixtures are described as filling the entireties of their respective cavities, it should be understood that small amounts of unfilled space will remain due to the inherent limitations of the applicable manufacturing processes. Also, it can be desirable to leave some space unfilled to facilitate placing the fixture into and removing the fixture from the cavity. Accordingly, the fixtures preferably fill "substantially all" of their respective cavities, which is hereby defined as filling 90% or more of a cavity.

Although described with reference to preferred embodiments of the invention, it should be readily understood that various changes and/or modifications could be made to the invention without departing from the spirit thereof. For example, while the cavity in this example has a cylindrical or cuboid shape, other shapes can be employed.

The invention claimed is:

1. A resonant system for measuring a dielectric constant of a sample comprising:
a device for holding a sample, the device including a resonant waveguide formed with a cavity configured to hold a fixture, the fixture being configured to hold a sample and fill substantially all of the cavity; and
a network analyzer including a signal source configured to send electromagnetic radiation toward a sample, a radio frequency detector configured to sense electromagnetic radiation reflected from or transmitted through a sample, and a processor configured to determine a dielectric constant of a sample based on the sensed electromagnetic radiation.

2. The system according to claim 1, wherein the fixture is plastic or ceramic.

3. The system according to claim 2, wherein the resonant waveguide is metal.

4. The system according to claim 2, wherein the fixture has a recess, the system further comprising a sample holder configured to hold a sample within the recess.

5. The system according to claim 2, further comprising a transmitting waveguide connected to the resonant waveguide, said transmitting waveguide having one coaxial port that is connected to one port on the network analyzer and being configured to capture electromagnetic radiation reflected from a sample.

6. The system according to claim 2, further comprising a transmitting waveguide connected to the resonant waveguide, said transmitting waveguide having two coaxial ports that are connected to two ports on the network analyzer and being configured to capture electromagnetic radiation transmitted through a sample.

7. The system according to claim 6, wherein the transmitting waveguide is rectangular and has a central aperture, and the resonant waveguide is circular and includes an aperture aligned with the central aperture.

8. The system according to claim 2, wherein the fixture is configured to hold a sample in a center of the cavity.

9. A method of determining a dielectric constant of a sample with a resonant system including a device for holding the sample and a network analyzer, the device including a resonant waveguide formed with a cavity configured to hold a fixture, said method comprising:
placing the sample in the fixture;
placing the fixture in the cavity;
sending electromagnetic radiation toward the sample;
sensing electromagnetic radiation reflected from or transmitted through the sample;

determining the dielectric constant of the sample based on the sensed electromagnetic radiation; and minimizing a size of the sample by changing a size or a geometry of the fixture.

10. The method of claim 9, wherein placing the sample in the fixture includes placing the sample in a plastic or ceramic fixture.

11. The method of claim 10, wherein placing the fixture in the cavity includes placing the fixture in a cavity of a metal resonant waveguide.

12. The method of claim 10, further comprising:

reducing a wavelength of the electromagnetic radiation with the fixture.

13. A method of determining a dielectric constant of a sample with a resonant system including a device for holding the sample and a network analyzer, the device including a resonant waveguide formed with a cavity configured to hold a fixture, said method comprising:

placing the sample in the fixture;

placing the fixture in the cavity;

sending electromagnetic radiation toward the sample;

sensing electromagnetic radiation reflected from or transmitted through the sample;

determining the dielectric constant of the sample based on the sensed electromagnetic radiation; and setting a frequency at which the resonant system determines the dielectric constant of the sample by changing a size or a geometry of the fixture.

14. The method of claim 13, further comprising:

minimizing a size of the sample by changing a size or a geometry of the fixture.

15. The method of claim 10, wherein the resonant system further comprises a transmitting waveguide connected to the resonant waveguide, said transmitting waveguide having one coaxial port that is connected to one port on the network analyzer, the method further comprising:

capturing electromagnetic radiation reflected from the sample with the transmitting waveguide.

16. The method of claim 10, wherein the resonant system further comprises a transmitting waveguide connected to the resonant waveguide, said transmitting waveguide having two coaxial ports that are connected to two ports on the network analyzer, the method further comprising:

capturing electromagnetic radiation transmitted through the sample with the transmitting waveguide.

17. The method of claim 10, further comprising:

placing the sample in a sample holder; and placing the sample holder in a recess of the fixture.

18. The method of claim 10, wherein placing the fixture in the cavity includes placing the fixture in the cavity so that the sample is in a center of the cavity.

19. The method of claim 9, wherein placing the fixture in the cavity includes placing the fixture in the cavity so that the fixture fills substantially all of the cavity.

20. The method of claim 13, wherein placing the fixture in the cavity includes placing the fixture in the cavity so that the fixture fills substantially all of the cavity.

* * * * *